United States Patent
Klahr et al.

(10) Patent No.: US 9,924,910 B2
(45) Date of Patent: Mar. 27, 2018

(54) 4D CONTRAST ENHANCED COMPUTED TOMOGRAPHY (CT)

(75) Inventors: Paul Harvey Klahr, Beachwood, OH (US); Ekta Dhawal Dharaiya, Twinsburg, OH (US); Scott Kenneth Pohlman, Willoughby, OH (US); Randall Peter Luhta, Chardon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 309 days.

(21) Appl. No.: 13/979,140

(22) PCT Filed: Jan. 11, 2012

(86) PCT No.: PCT/IB2012/050133
§ 371 (c)(1),
(2), (4) Date: Sep. 23, 2013

(87) PCT Pub. No.: WO2012/095797
PCT Pub. Date: Jul. 19, 2012

(65) Prior Publication Data
US 2014/0018672 A1    Jan. 16, 2014

Related U.S. Application Data

(60) Provisional application No. 61/432,906, filed on Jan. 14, 2011.

(51) Int. Cl.
*A61B 6/00*    (2006.01)
*A61N 5/00*    (2006.01)
(Continued)

(52) U.S. Cl.
CPC ............ *A61B 6/032* (2013.01); *A61B 6/04* (2013.01); *A61B 6/0457* (2013.01); *A61B 6/405* (2013.01);
(Continued)

(58) Field of Classification Search
CPC combination set(s) only.
See application file for complete search history.

(56) References Cited

U.S. PATENT DOCUMENTS 7,042,975 B2    5/2006 Heuscher
7,418,075 B2    8/2008 Taguchi
(Continued)

OTHER PUBLICATIONS

Cai et al., "Dose Reduction with Adaptive Bolus Chasing Computed Tomography Angiography", J Xray Sci Technol. Jan. 1, 2010; 18(1): 15-25.*

(Continued)

*Primary Examiner* — Serkan Akar
*Assistant Examiner* — Farshad Negarestan

(57) ABSTRACT

A method includes performing a contrast enhanced computed tomography (CT) scan of tissue of interest of a subject, with an imaging system (100) having a radiation source (112) and a detector array (118), in which a peak contrast enhancement of the tissue of interest, a full range of motion of the tissue of interest, and an entire volume of interest of the tissue of interest are concurrently imaged during a single rotation of the radiation source and the detector array of the imaging system over an entire or a predetermined sub-portion of a breathing cycle.

12 Claims, 3 Drawing Sheets

(51) Int. Cl.

| | | |
|---|---|---|
| *A61B 6/03* | (2006.01) | |
| *A61B 6/04* | (2006.01) | |
| *B32B 3/26* | (2006.01) | |
| *B32B 3/30* | (2006.01) | |
| *B32B 5/18* | (2006.01) | |
| *B32B 7/12* | (2006.01) | |
| *B32B 7/14* | (2006.01) | |
| *B32B 27/12* | (2006.01) | |
| *A61M 5/00* | (2006.01) | |
| *A61N 5/10* | (2006.01) | |

(52) U.S. Cl.
CPC .......... *A61B 6/4085* (2013.01); *A61B 6/4275* (2013.01); *A61B 6/481* (2013.01); *A61B 6/482* (2013.01); *A61B 6/507* (2013.01); *A61B 6/541* (2013.01); *A61M 5/007* (2013.01); *A61N 5/1037* (2013.01); *A61N 5/1039* (2013.01); *B32B 3/266* (2013.01); *B32B 3/30* (2013.01); *B32B 5/18* (2013.01); *B32B 7/12* (2013.01); *B32B 7/14* (2013.01); *B32B 27/12* (2013.01); *A61N 5/103* (2013.01); *B32B 2262/02* (2013.01); *Y10T 156/1041* (2015.01); *Y10T 156/1057* (2015.01); *Y10T 428/15* (2015.01); *Y10T 428/24322* (2015.01); *Y10T 428/24496* (2015.01); *Y10T 428/24504* (2015.01); *Y10T 428/24851* (2015.01); *Y10T 428/24995* (2015.04); *Y10T 428/249953* (2015.04); *Y10T 428/249982* (2015.04); *Y10T 428/249985* (2015.04); *Y10T 428/249987* (2015.04); *Y10T 428/249991* (2015.04); *Y10T 428/249992* (2015.04); *Y10T 428/249993* (2015.04)

(56) References Cited

U.S. PATENT DOCUMENTS

| | | |
|---|---|---|
| 7,522,696 B2 | 4/2009 | Imai |
| 2005/0084060 A1* | 4/2005 | Seppi et al. .................... 378/5 |
| 2006/0247518 A1 | 11/2006 | Boing et al. |
| 2010/0104062 A1 | 4/2010 | Wu et al. |
| 2010/0135454 A1 | 6/2010 | Noo |

OTHER PUBLICATIONS

Saw, et al.,. A review on the clinical implementation of Respiratory-gated radiation therapy, Biomedical Imaging and Intervention Journal Review Article, 2007, 8 sheets, vol. 3, No. 1.

Beddar, et al., 4D-CT imaging with synchronized intravenous contrast injection to improve delineation of liver tumors for treatment planning, Radiotherapy and Oncology, 2008, pp. 445-448, vol. 87.

McNamaa, et al, investigation of two respiratory monitoring system used for 4D CT and respiratory gating,1919 University of Wollongong Thesis Collection, 2008, 19 sheets.

Mori, S., et al.; Clinical Potentials for Dynamic Contrast-enhanced Hepatic Volumetric Cine Imaging with the Prototype 256-MDCT Scanner; 2005; American Journal of Roentgenology; 185(1)253-256.

Mori, S., et al.; Four-dimensional measurement of lung tumor displacement using 256-multi-slice CT-scanner; 2007; Lung Cancer; 56:59-67.

* cited by examiner

4D CONTRAST ENHANCED COMPUTED TOMOGRAPHY (CT)

CROSS REFERENCE TO RELATED APPLICATIONS

This application is a national filing of PCT application Ser. No. PCT/IB2012/050133, filed Jan. 11, 2012, published as WO 2012/095797 A2 on Jul. 19, 2012, which claims the benefit of U.S. provisional application Ser. No. 61/432,906 filed Jan. 14, 2011, which is incorporated herein by reference.

FIELD OF THE INVENTION

The following generally relates to imaging and more particularly to 4D computed tomography (CT) with contrast enhancement, and is described with particular application to radiation treatment planning.

BACKGROUND OF THE INVENTION

Oncology treatment planning is the process creating a treatment plan for treating a tumor(s) with radiation therapy (i.e., ionizing radiation), surgery, chemotherapy, etc. Generally, for treatment planning, the subject is scanned (e.g., via a computed tomography (CT) or other scanner) and the resulting volumetric image data is used to run treatment simulations and/or create the treatment plan. However, it is often difficult to visualize a tumor, which may be moving due to respiratory and/or cardiac motion, in the image data without contrast. As such, a contrast-enhanced CT scan is typically performed.

With a scanner having a z-axis detector coverage of about two and a half centimeters (2.5 cm) per rotation, a scan from the shoulders to the hips may cover about fifty centimeters (50 cm), and where each couch position is scanned over an entire breathing cycle (e.g., about four seconds (4 s) from full inhalation to full exhalation), the scan will take about eighty seconds (80 s) to perform. Such a scan may be a low-pitch free-breathing respiratory-gated helical-CT scan in which each rotation covers the entire respiratory cycle for a number of rotations required to image the entire tumor, or a series of axial scans at different couch increments in which at each couch position the patient is scanned over the entire respiratory cycle and where the axial slices are combined together to form volumetric data covering the entire tumor.

For such a scan, a scout or low dose scan is first performed to localize the tumor in the subject in order to determine proper positioning of the subject to scan the tumor. In this example, a test bolus is administered to the subject in order to determine an approximated time to peak contrast uptake in the tissue of interest. Other approaches may also be utilized to approximate the time to peak contrast uptake. In addition, the respiratory cycle of the patient is monitored with a bellow belt or other device. The subject is positioned based on the localization, and the monitored respiratory cycle and the approximated time to peak contrast uptake are then used to gate contrast enhanced scanning in an attempt to capture peak contrast uptake in the tissue.

Unfortunately, it may be difficult to synchronize the timing of the scan with peak contrast uptake and enhancement of the tumor. As such, peak contrast uptake may be missed, in part or entirely, and the subject may have to be re-scanned one or more times to capture desired contrast enhancement for treatment planning. As a consequence, the patient may be exposed to multiple doses of contrast material and/or multiple scans and radiation exposure.

SUMMARY OF THE INVENTION

Aspects of the present application address the above-referenced matters and others.

According to one aspect, a method includes performing a contrast enhanced computed tomography (CT) scan of tissue of interest of a subject, with an imaging system having a radiation source and a detector array, in which a peak contrast enhancement of the tissue of interest, a full range of motion of the tissue of interest, and an entire volume of interest of the tissue of interest are concurrently imaged during a single rotation of the radiation source and the detector array of the imaging system.

According to another aspect, an imaging system includes a radiation source that rotates around an examination region about a z-axis and emits radiation that traverses the examination region and a detector array, located across the examination region, opposite the radiation source, that detects radiation traversing the examination region. The detector array includes a plurality of rows of detectors along the z-axis direction providing a z-axis coverage, and the coverage is such that an entire volume of interest of moving tissue of interest is scanned during a single revolution of the source. The scan is performed during the single revolution and covers a complete moving cycle of the tissue of interest, and the scan images a peak contrast uptake of contrast material by the tissue of interest during the revolution. The system further includes a reconstructor that reconstructs a four dimensional contrast enhanced data set based on the scan.

According to another aspect, a method includes localizing a scan around a region of interest, scanning, with zero pitch, the region of interest during peak contrast uptake of a tumor within the region of interest such that the tumor is maintained within a scan field of view during its full range of motion, and obtaining a four dimensional contrast enhanced image of the region of interest, including the tumor.

According to another aspect, a method includes synchronizing translation of a subject support carrying a patient being scanned and an estimated time to peak contrast enhancement of tissue of interest of the patient so that peak contrast enhancement occurs in the tissue of interest when the tissue of interest is being scanned and the tissue of interest is imaged over a full range of motion of the tissue of interest with respect to the patient.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
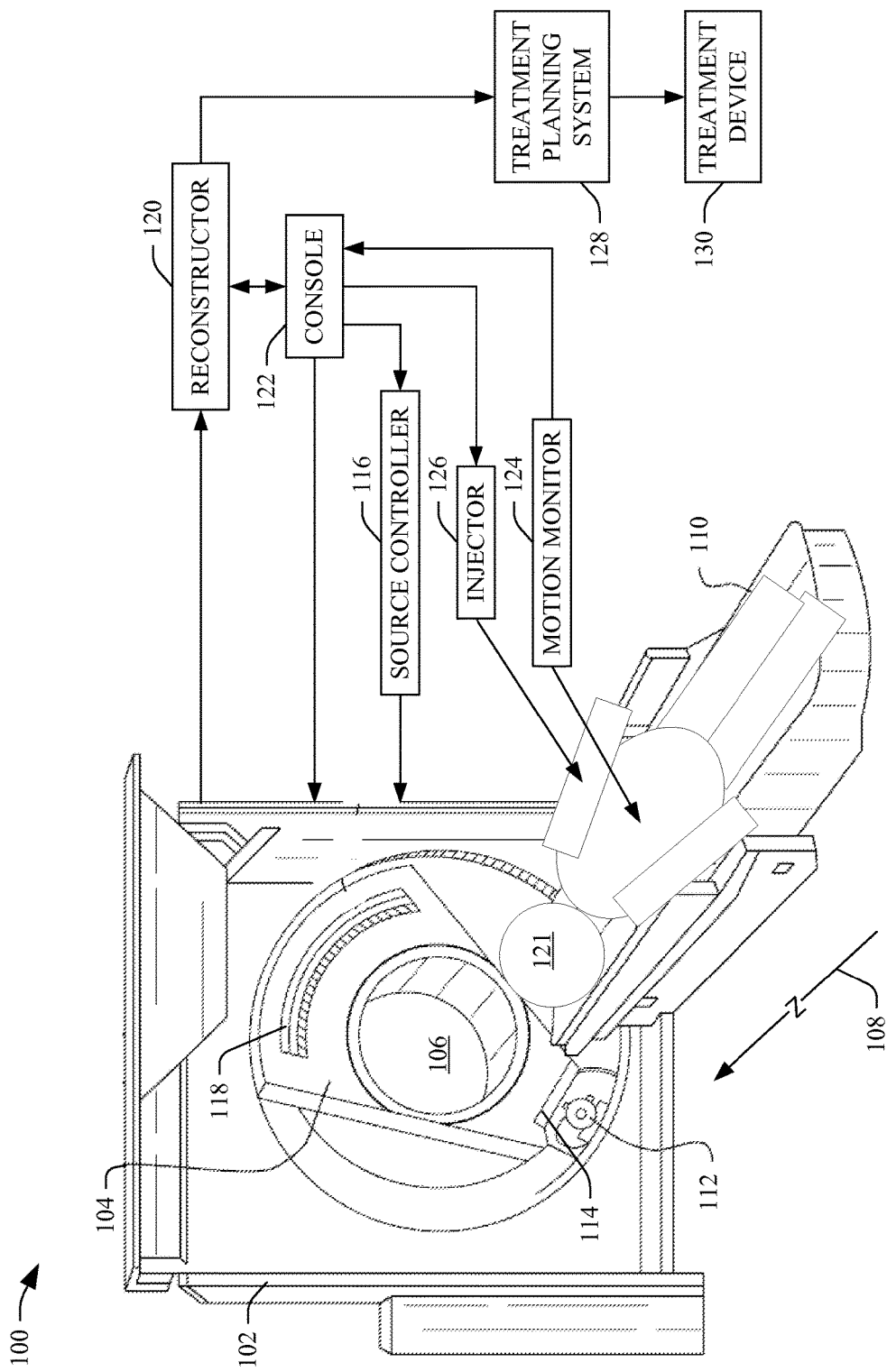
FIG. 1 schematically illustrates an imaging system in connection with a treatment planning system and a treatment device.

FIG. 1 schematically illustrates an imaging system such as a computed tomography (CT) scanner 100.

The scanner 100 includes a stationary gantry 102 and a rotating gantry 104, which is rotatably supported by the stationary gantry 102. The rotating gantry 104 rotates around an examination region 106 about a longitudinal or z-axis 108 one or more times for one or more data acquisition cycles.

A radiation source 112, such as an x-ray tube, is supported by and rotates with the rotating gantry 104 around the examination region 106. The illustrated radiation source 112 is configured to produce x-radiation corresponding to a plurality of different peak voltages. A source collimator 114 collimates the emitted radiation to produce a generally fan, wedge, or cone shaped radiation beam that traverses the examination region 106.

A source controller 116 controls an emission spectrum of the radiation source 112. The illustrated controller 116 is configured so that it can optionally switch the radiation source 112 voltage between at least two different peak voltages during scanning. By way of non-limiting example, in one instance the controller 116 can switch the source voltage between 80 kVp and 140 kVp (or other desired spectral difference, including more than two different voltages). In one instance, the controller 116 does not switch the kVp.

A radiation sensitive detector array 118 detects radiation that traverses the examination region 106 and generates a signal (projection data) indicative of the detected radiation. The illustrated detector array 118 includes a two dimensional (2D) array of detectors having a plurality of rows of detectors arranged with respect to each other in the z-axis direction.

In non-limiting one instance, the scan coverage along the z-axis for a single rotation is in a range from about five centimeters (5 cm) to about twenty centimeters (20 cm), for example, about eight centimeters (8 cm), about ten centimeters (10 cm), etc. Other z-axis coverage (greater or less) is also contemplated herein. Furthermore, in jog mode, in which the scanner can move back and forth, the scan coverage is effectively doubled (e.g., 8 cm in one direction and 8 cm in the other direction, or 16 cm total). Such coverage may correspond to a geometry of tissue of interest such as a tumor in the liver, the lungs, etc., or other anatomical tissue of interest in a subject.

By way of example, where the imaging system 100 is configured to generate image data used for treatment planning and/or treatment therapy, the detector array 118 can be configured to image the entire or a predetermined volume or sub-portion of the tissue of interest without having to move the subject relative to the z-axis during scanning the patient. For instance, for a three centimeter (3 cm) tumor (typical tumor size is about three to five centimeters (3-5 cm)) that moves within a patient about two centimeters (2 cm), for example, due to breathing, an eight centimeter (8 cm) z-axis coverage would allow for imaging the entire tumor, including during the movement of the tumor without moving the patient.

In another example, where the entire or a predetermined volume or sub-portion of the tissue of interest cannot be imaged without translating the subject along the z-axis through the examination region 106 during scanning the patient, for example, where the z-axis scan coverage for a single rotation is in a range from about one centimeters (1 cm) to about four centimeters (4 cm), contrast administration is synchronized with translation of the subject such that both the tissue of interest during its movement cycle and peak contrast uptake in the tissue of interest are concurrently imaged.

A patient support 110, such as a couch, supports a patient 121 in the examination region 106. For example, the patient support 110 can be used to position the patient for any pre-scan. The patient support 110 can also be used to position the patient such that the tissue of interest is between the radiation source and the detector array and in the examination region for a zero pitch contrast enhanced scan in which the entire tissue of interest is scanned over its entire range of motion.

A reconstructor 120 reconstructs the signal from the detector array 118 and generates volumetric image data indicative of the examination region 106. The reconstructor 120 can employ various reconstruction algorithms. For example, in one instance the reconstructor 120 employs a 4D algorithm and generates a 4D data set based on data acquired at different timeframes. In the case of contrast enhanced image data, the image data corresponding to different timeframes may have different contrast enhancement representing different states of contrast uptake and wash out in tissue during scanning.

The reconstructor 120 can also employ a multi-energy reconstruction algorithm to generate an image for one or more individual energy ranges (tube peak voltages) and/or a composite image covering two or more of the energy ranges. A comparison of images corresponding to different emission spectrums may be used to differentiate between the atomic or elemental compositions of tissue of interest, other tissue, and/or contrast material. Other suitable reconstruction algorithms include 2D and/or 3D reconstruction algorithms.

A general purpose computing system serves as an operator console 122, and includes an output device such as a display and an input device such as a keyboard, mouse, and/or the like. The console 122 includes one or more processors that execute one or more computer readable instructions encoded on computer readable storage medium. Additionally or alternatively, the one or more computer readable instructions can be carried by a signal, a carrier wave or the like.

In one instance, the executing instructions provide a user interactive interface through which a clinician or other authorized user can control operation of the system 100, for example, for scanning by allowing the clinician to select a pre-scan (scout or low dose axial or helical scan) and subsequently a scan protocol such as a single or multi-energy scan protocol, a contrast enhanced protocol, a respiratory cycle and/or contrast enhancement gated scan protocol, a zero pitch helical scan protocol, a combination thereof and/or another scan protocol.

A motion sensor or monitor 124 is configured to sense a motion state of at least a predetermined volume of interest of a moving object or subject in the examination region 106 and generate a signal indicative thereof. The motion monitor 124 may include a respiratory, a cardiac, and/or other motion sensor. For respiratory applications, the motion monitor 124 may include a respiratory bellows belt, fiduciary markers, or the like. The output signal of the illustrated monitor 124 is provided to the console 122, which may utilize the output signal to gate scanning, gate contrast material administration, map the respiratory cycle to the reconstructed image data, a combination thereof, and/or otherwise.

An injector 126 is configured to inject a contrast material(s), for example, for a contrast enhanced imaging procedure. The illustrated injector 126 is controlled by the console 122, which may trigger or invoke in the injector 126 to administer the contrast material in coordination with invoking scanning such that peak contrast uptake and enhancement by tissue of interest is scanned during a single respiratory cycle. A contrast agent can additionally or alternatively be manually administered by a clinician or the like. Where the contrast agent is manually administered, the injector 126 can be omitted.

The illustrated imaging system 100 is used in connection with a treatment planning system 128 and a treatment device 130. The treatment planning system 128 can be used to simulate treatment response to treatment and generate treatment plans for the treatment device 130 based on the image data from the imaging system 100, such as a 4D contrast enhanced image data set. Additionally or alternatively, the treatment planning system 128 can use information from other imaging modalities and/or other image data for generating a treatment plan. The treatment device 130 may be configured for implementing radiation therapy (external beam, brachytherapy, etc.), chemotherapy, particle (e.g., proton) therapy, high intensity focused ultrasound (HIFU), ablation, a combination thereof and/or other treatment.

Figure 2:
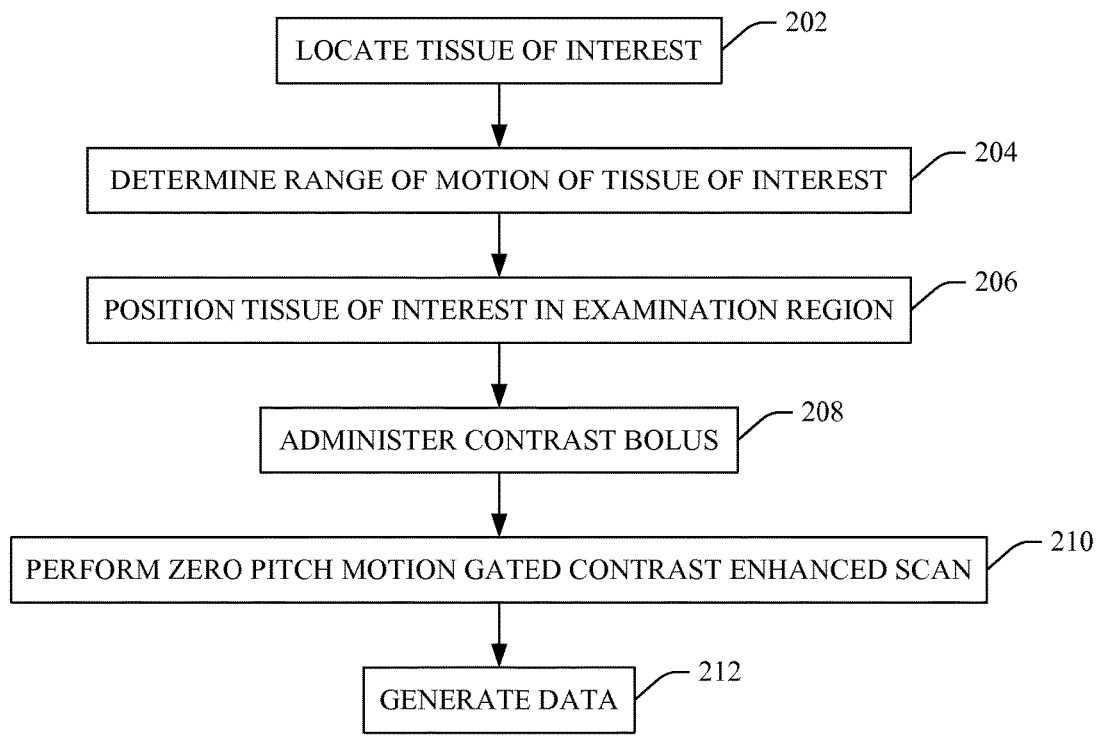
FIG. 2 illustrates an example method for generating a 4D contrast enhanced data set of tissue of interest over a range of motion of the tissue of interest during a motion cycle of the tissue of interest without having to synchronize the timing of the scan over the tissue of interest during peak contrast enhancement while imaging over a single rotation.

FIG. 2 illustrates an example method for generating a 4D contrast enhanced data set of tissue of interest over a range of motion of the tissue of interest during a motion cycle of the tissue of interest without having to synchronize the timing of the scan over the tissue of interest during peak contrast enhancement while imaging over a single rotation.

It is to be appreciated that the ordering of the acts in the methods described herein is not limiting. As such, other orderings are contemplated herein. In addition, one or more acts may be omitted and/or one or more additional acts may be included.

At 202, a location of tissue of interest of a subject is identified. For example, in one instance an approximate location of a tumor in the liver, lung, and/or other anatomical structure of the patient is identified. The approximate location can be determined by performing a pre-scan such as a scout scan, a low dose helical scan, and/or other pre-scan, and identifying the location of the tissue of interest of the subject based on the image(s) from the pre-scan.

At 204, a range of motion of the portion of the tissue of interest is determined. As discussed herein, where the relative location of the tissue of interest in the patient varies with the respiratory (and/or the heart) cycle, the respiratory (and/or the heart) cycle can be monitored via a bellows belt or other respiratory monitoring device. The range of motion can be determined based on the monitored cycle synchronized with imaging data from a scan of the patient. Alternatively, the respiratory cycle and/or the cardiac cycle can be used.

At 206, the patient is positioned in the examination region such that a portion (the entire or a sub-portion of) the tissue of interest is in the examination region in the path of the radiation from the radiation source to the detector array for the determined range of motion. Where the detector array z-axis coverage is about five to twenty centimeters (5-20 cm), the patient can be positioned in the examination region such that the entire portion of the tissue of interest is within the coverage of the detector array. Of course, the patient can be position such that the entire portion of the tissue of interest is not within the coverage of the detector array, if desired so by the clinician.

At 208, a bolus of contrast is administered to the patient. The bolus can be administered before, concurrently with, or after scanning begins, depending on an estimated time to peak uptake for the tissue of interest, which can be determined through a test bolus and a pre-scan, previous contrast enhanced scans for the patient and/or other patients, and/or otherwise. The timing of the bolus need not be synchronized with the timing of the scanning in order to image the portion of the tissue of interest during peak contrast enhancement.

At 210, a zero pitch gated helical scan is performed in which the scan is gated in coordination the respiratory cycle such that the tissue of interest is entirely imaged in a single rotation and over a portion of the determined motion range or respiratory cycle (including the complete cycle or a sub-set thereof) covering the motion range of the tissue of interest. The timing of the gating need not be synchronized with the timing of the bolus in order to image the portion of the tissue of interest during peak contrast enhancement.

At 212, a 4D contrast enhanced data set is generated based on the scan. Such a data set shows contrast enhancement of the portion of the tissue of interest over the motion range and can be used to facilitate treatment planning. Additionally or alternatively, the 4D data may visually provide perfusion information. Additionally or alternatively, the 4D data may be used to generate contrast maps, for example, where a multi-energy (kVp) scan is performed.

The above may be implemented by way of computer readable instructions, which when executed by a computer processor(s), cause the processor(s) to carry out the described acts. In such a case, the instructions are stored in a computer readable storage medium associated with or otherwise accessible to the relevant computer.

Figure 3:
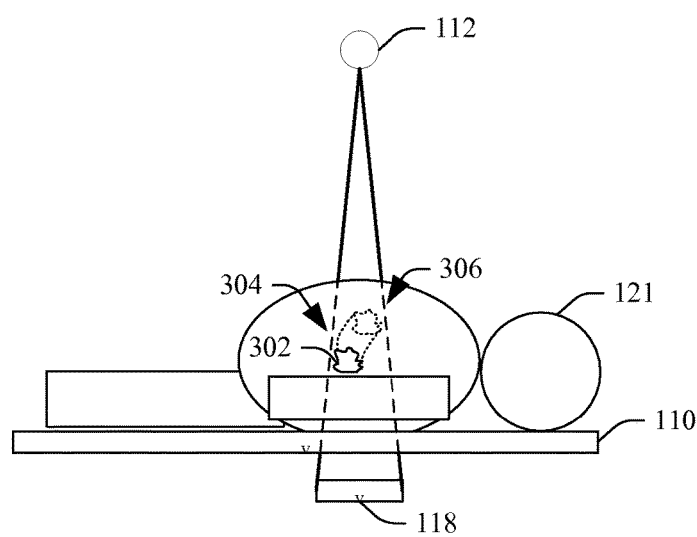
FIG. 3 illustrates an example showing positioning of a tissue of interest in connection with the system of FIG. 1.

FIG. 3 shows an example in which the patient 121 is positioned in the path of the radiation beam from the source 112 to the detector array 118 via the patient support 110. In this embodiment, the patient 121 is positioned such that the tissue of interest 302 remains in the radiation path and is imaged during at least one rotation of the source 112, although the tissue of interest may move between first and second locations 304 and 306 within the beam, for example, due to respiratory, cardiac, and/or other motion.

Using such an approach mitigates having to synchronize scanning with contrast administration to ensure imaging of peak contrast uptake and enhancement as the entire tissue of interest 302 is imaged the entire time. In an alternative configuration, in which the a helical or step and shoot axial scan has to the performed to capture the entire tissue of interest, synchronization of scanning with contrast administration may be required in order to ensure peak contrast uptake and enhancement of the tissue of interest is not missed as the entire volume of the tissue of interest is not scanned the entire time during scanning.

Figure 4:
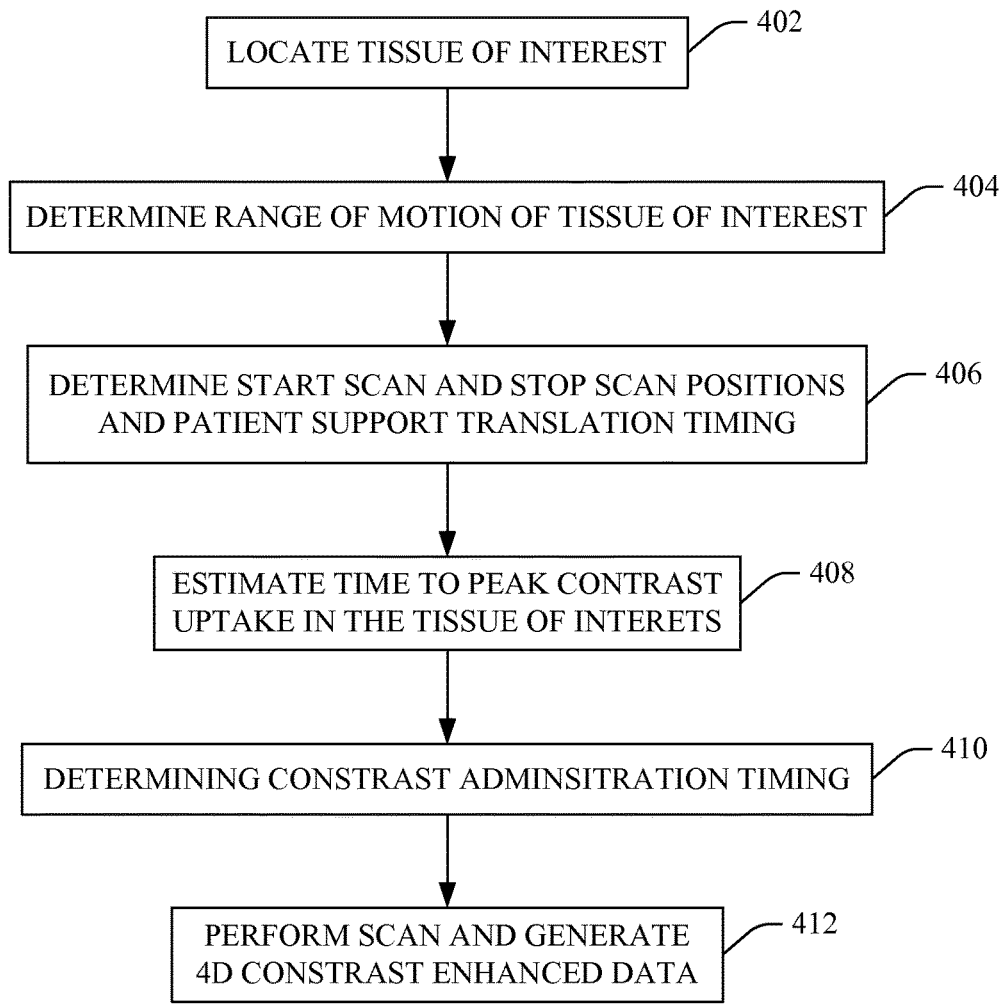
FIG. 4 illustrates an example method for generating a 4D contrast enhanced data set of tissue of interest over a range of motion of the tissue of interest during a motion cycle of the tissue of interest via synchronizing administration of contrast and translation of patent during scanning to image the tissue of interest over its entire movement cycle and capture peak contrast uptake in the tissue of interest.

FIG. 4 illustrates an example method for generating a 4D contrast enhanced data set of tissue of interest over a range of motion of the tissue of interest during a motion cycle of the tissue of interest via synchronizing administration of contrast and translation of the patent (via the subject support 110) during scanning to image the tissue of interest over its entire movement cycle and capture peak contrast uptake in the tissue of interest.

It is to be appreciated that the ordering of the acts in the methods described herein is not limiting. As such, other orderings are contemplated herein. In addition, one or more acts may be omitted and/or one or more additional acts may be included.

At 402, a location of tissue of interest of a subject is identified. For example, in one instance an approximate location of a tumor in the liver, lung, and/or other anatomical structure of the patient is identified. The approximate location can be determined by performing a pre-scan such as a scout scan, a low dose helical scan, and/or other pre-scan, and identifying the location of the tissue of interest of the subject based on the image(s) from the pre-scan.

At 404, a range of motion of the portion of the tissue of interest is determined. As discussed herein, where the relative location of the tissue of interest in the patient varies with the respiratory (and/or the heart) cycle, the respiratory (and/or the heart) cycle can be monitored via a bellows belt or other respiratory monitoring device. The range of motion can be determined based on the monitored cycle synchronized with imaging data from a scan of the patient. Alternatively, the respiratory cycle and/or the cardiac cycle can be used.

At 406, a scan plan, including a start scan position and a stop scan position (or z-axis extent) and patient support translation timing, is determined based on the location of the tissue of interest and the range of motion such that the entire tissue of interest is imaged during its entire range of motion during a single revolution of the radiation source 112.

At 408, a time to peak contrast uptake of the tissue of interest is estimated. This may include performing a pre-scan in which a test bolus of contrast is administered to the patient to determine approximately the length of time between administration and peak contrast uptake. Alternatively, such information can be estimated based on previously performed imaging procedures of the subject and/or other subjects, a model, and/or otherwise.

At 410, contrast administration timing with the scan is determined based on the scan plan (i.e., the time at which the subject support positions the tissue of interest in the examination region) and the time to peak contrast uptake such that peak contrast uptake in the tissue of interest is imaged concurrently with the tissue of interest during the single revolution of the radiation source 112. It is to be appreciated that contrast administration may occur before, concurrently with, or after scanning begins, depending on both the time to peak contrast uptake and the time at which the subject support positions the tissue of interest in the examination region.

At 412, the imaging examination, including contrast administration and scanning, is performed, and a 4D contrast enhanced data set, capturing peak contrast uptake in the tissue of interest and the tissue of interest over the entire movement cycle of the tissue of interest, is generated.

With this method, subject support translation and contrast uptake are synchronized to ensure peak uptake occurs in the field of view while acquiring a traditional four dimensional scan covering the tissue of interest over the full motion range of the tissue of interest.

The methods described herein can be implemented by way of computer readable instructions, which when executed by a computer processor(s), cause the processor(s) to carry out the described acts. In such a case, the instructions are stored in a computer readable storage medium associated with or otherwise accessible to the relevant computer.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:
monitoring a motion cycle of a subject during a low dose scan or a scout scan of a tissue of interest of the subject;
determining locations of an entire volume of interest of the tissue of interest with respect to the motion cycle, wherein the tissue of interest moves in coordination with the motion cycle over a full range of motion according to the motion cycle, wherein the locations are identified according to z-extents over the motion cycle of the entire volume of interest in the low dose scan or the scout scan;
positioning the subject in an examination region of an imaging system based on the determined locations, wherein the entire volume of interest of the tissue of interest is maintained in the examination region during scanning by the imaging system as the tissue of interest moves between the z-extents in coordination with the motion cycle for a single rotation of a radiation source and a detector array of the imaging system;
determining an estimated time to peak uptake of a bolus of contrast for the tissue of interest; and
performing a motion gated contrast enhanced computed tomography (CT) scan of the tissue of interest of the subject, with the imaging system having the radiation source and the detector array, before, concurrently with, or after administration of the bolus of contrast depending on the estimated time to peak uptake for the tissue of interest, wherein a peak contrast enhancement of the tissue of interest, a full range of motion of the tissue of interest, and the entire volume of interest of the tissue of interest are concurrently imaged during the single rotation of the radiation source and the detector array of the imaging system.

2. The method of claim 1, wherein the scan is a zero pitch helical scan.

3. The method of claim 1, wherein the scan is performed without having to synchronize a timing of the scan with contrast administration in order to image the peak contrast enhancement of the tissue of interest.

4. The method of claim 1, wherein the imaging system also includes a patient support for supporting the subject during the scan, wherein the scan is performed with the patient support and hence the subject at a same relative location with respect to the imaging system during the scan.

5. The method of claim 1, wherein a z-axis scan coverage of the detector array for the rotation is at least as large as the volume of interest of the tissue of interest.

6. The method of claim 1, wherein a z-axis scan coverage of the detector array for the rotation is in a range of about five centimeters to about twenty centimeters.

7. The method of claim 1, further comprising:
reconstructing a four dimensional contrast enhanced data set based on an output of the scan; and
planning a treatment procedure based on the four dimensional contrast enhanced data set.

8. The method of claim 1, further comprising:
reconstructing a four dimensional perfusion data set that provides visual information indicative of a perfusion of the contrast material through the tissue of interest during the rotation.

9. The method of claim 1, wherein the scan is a multi-energy scan in which the radiation source is switched between at least two different peak voltages during the rotation, and further comprising:

generating at least one spectral image based on data corresponding to only one of the peak voltages.

10. The method of claim 9, wherein the at least one spectral image provides a contrast material map.

11. The method of claim 10, further comprising:
simulating a response to treatment based on the contrast material map.

12. The method according to claim 1, wherein performing includes imaging the entire volume of interest over the full range of motion during the performed contrast enhanced CT scan in the single rotation of the radiation source and the detector array.

* * * * *